(12) United States Patent
Nakamura

(10) Patent No.: US 11,062,448 B2
(45) Date of Patent: Jul. 13, 2021

(54) MACHINE LEARNING DATA GENERATION SUPPORT APPARATUS, OPERATION METHOD OF MACHINE LEARNING DATA GENERATION SUPPORT APPARATUS, AND MACHINE LEARNING DATA GENERATION SUPPORT PROGRAM

(71) Applicant: FUJIFILM Corporation, Tokyo (JP)

(72) Inventor: Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 39 days.

(21) Appl. No.: 16/042,292

(22) Filed: Jul. 23, 2018

(65) Prior Publication Data

US 2019/0057503 A1 Feb. 21, 2019

(30) Foreign Application Priority Data

Aug. 17, 2017 (JP) ............................. JP2017-157672

(51) Int. Cl.
*G06T 7/00* (2017.01)
*G16H 30/40* (2018.01)
*G06F 16/58* (2019.01)
*G06F 16/9032* (2019.01)
*G06F 16/903* (2019.01)
(Continued)

(52) U.S. Cl.
CPC ........ *G06T 7/0014* (2013.01); *G06F 16/5866* (2019.01); *G06F 16/90332* (2019.01); *G06F 16/90344* (2019.01); *G06T 7/0012* (2013.01); *G16H 15/00* (2018.01); *G16H 30/20* (2018.01); *G16H 30/40* (2018.01); *G16H 40/63* (2018.01); *G16H 50/20* (2018.01);
(Continued)

(58) Field of Classification Search
CPC .............................. G06F 19/321; G16H 30/20
USPC ......... 705/3, 2; 707/767, 758; 382/224, 131, 382/132, 128, 133
See application file for complete search history.

(56) References Cited

U.S. PATENT DOCUMENTS

2008/0052126 A1 2/2008 Sasai et al.
2008/0123927 A1* 5/2008 Miga ...................... G06T 7/344
382/131
(Continued)

FOREIGN PATENT DOCUMENTS

JP 2006-155002 A 6/2006
JP 2008-52544 A 3/2008
(Continued)

OTHER PUBLICATIONS

Japanese Office Action for Japanese Application No. 2017-157672, dated Aug. 4, 2020, with English translation.

*Primary Examiner* — Kiet M Doan
(74) *Attorney, Agent, or Firm* — Birch, Stewart, Kolasch & Birch, LLP

(57) ABSTRACT

Retrieval means analyzes character strings of a plurality of interpretation reports to retrieve an interpretation report in which a retrieval keyword is included. Registration means performs image processing with respect to a medical image corresponding to the retrieved interpretation report, extracts an anatomic region related to the retrieval keyword, and registers information indicating the anatomic region and the medical image as correct answer data in a case where the size of the extracted anatomic region is different from a standard size of the anatomic region or in a case where the shape of the extracted anatomic region is different from a standard shape of the anatomic region.

14 Claims, 21 Drawing Sheets

(51) Int. Cl.
*G16H 40/63* (2018.01)
*G16H 15/00* (2018.01)
*G16H 50/20* (2018.01)
*G16H 30/20* (2018.01)

(52) U.S. Cl.
CPC .............. *G06T 2207/10081* (2013.01); *G06T 2207/10088* (2013.01); *G06T 2207/10116* (2013.01); *G06T 2207/10132* (2013.01); *G06T 2207/30028* (2013.01); *G06T 2207/30048* (2013.01); *G06T 2207/30056* (2013.01); *G06T 2207/30061* (2013.01); *G06T 2207/30084* (2013.01); *G06T 2207/30096* (2013.01)

(56) References Cited

U.S. PATENT DOCUMENTS

| | | | |
|---|---|---|---|
| 2011/0019886 A1 | 1/2011 | Mizuno | |
| 2015/0065589 A1* | 3/2015 | Lenges | C08J 11/04 521/47 |
| 2015/0262014 A1* | 9/2015 | Iwamura | G06T 7/70 382/128 |
| 2015/0317434 A1* | 11/2015 | Kondo | G06F 16/24 705/3 |
| 2017/0053039 A1* | 2/2017 | Takeuchi | G06F 16/242 |
| 2017/0337329 A1* | 11/2017 | Liu | G06F 19/321 |
| 2018/0240237 A1* | 8/2018 | Donhowe | A61B 34/30 |
| 2019/0013093 A1* | 1/2019 | Slepian | G16H 10/60 |

FOREIGN PATENT DOCUMENTS

| | | |
|---|---|---|
| JP | 2011-24799 A | 2/2011 |
| JP | 2015-187845 A | 10/2015 |

\* cited by examiner

FIG. 3

| PATIENT NAME: ○○×× |
| INSPECTION ID: CTxxxx |
| IMAGING DATE: xx/yy/zz |

DOCTOR'S OPINION (DOCTOR'S OPINION SENTENCE INPUT REGION)

THE LIVER

F-1 THE LEFT LOBE OF THE LIVER IS LIGHTLY TUMEFACIENT.
THE MARGIN IS SHARP, THE SURFACE IS SMOOTH, THE ATROPHY IS NOT PRESENT, THE SUBSTANCE IS UNIFORM, AND THE CONCENTRATION IS NORMAL.

REPORT EDITING SCREEN

| LIVER | BILE DUCTS | GALL BLADDER | PANCREAS | SPLEEN | ADRENAL | GLAND | ENTIRE ABDOMEN |

| SHAPE OF LIVER | TUMEFACIENT LESION | CALCIFICATION | ENTIRE LIVER |
|---|---|---|---|
| MARGIN | SHARP | SLIGHTLY DULL | DULL |
| SURFACE | SMOOTH | SLIGHTLY IRREGULAR | IRREGULAR |
| TUMEFACTION | DEGREE | NON | LIGHT | MODERATE | HIGH |
|  | PORTION | ENTIRE LIVER | RIGHT LOBE | LEFT LOBE |  |
| ATROPHY | DEGREE | NON | LIGHT | MODERATE | HIGH |
|  | PORTION | ENTIRE LIVER | RIGHT LOBE | LEFT LOBE |  |
| SUBSTANCE | UNIFORMITY | UNIFORM | NOT-UNIFORM |
|  | CONCENTRATION | LOW | NORMAL | HIGH |

[ ADD DOCTOR'S OPINION ] [ END ] [ STOP ] [ CANCEL ]

FIG. 4A

| ORGAN | DOCTOR'S OPINION ITEM | DOCTOR'S OPINION ELEMENT | |
|---|---|---|---|
| LIVER | SHAPE OF LIVER | MARGIN | |
| | | SURFACE | |
| | | TUMEFACTION | PORTION |
| | | | DEGREE |
| | | ATROPHY | PORTION |
| | | | DEGREE |
| | | SUBSTANCE | UNIFORMITY |
| | | | CONCENTRATION |
| | TUMEFACTINE LESION | ... | |
| | CALCIFICATION | ... | |
| | ENTIRE LIVER | ... | |
| BILE DUCTS | ... | ... | |
| GALL BLADDER | ... | ... | |
| ⋮ | ⋮ | ⋮ | |

FIG. 4B

| | DOCTOR'S OPINION ELEMENT-MARGIN | | | | |
|---|---|---|---|---|---|
| TYPE | TERM SELECTION BUTTON | USAGE POSITION | USAGE FORMAT | DIFFERENTIATION INFORMATION | EXPRESSION |
| FIXED | | | | | MARGIN |
| INPUT | SHARP | | | NORMAL | SHARP |
| | SLIGHTLY DULL | | | ABNORMAL | SLIGHTLY DULL |
| | DULL | | | ABNORMAL | DULL |
| VARIABLE | | MIDDLE | POSITIVE | | "," |
| | | END | POSITIVE | | "IS-." |

FIG. 4C

| \\ | DOCTOR'S OPINION ELEMENT-SURFACE ||||||
|---|---|---|---|---|---|
| TYPE | TERM SELECTION BUTTON | USAGE POSITION | USAGE FORMAT | DIFFERENTIATION INFORMATION | EXPRESSION |
| FIXED | | | | | SURFACE |
| INPUT | SMOOTH | | | NORMAL | SMOOTH |
| | SLIGHTLY IRREGULAR | | | ABNORMAL | SLIGHTLY IRREGULAR |
| | IRREGULAR | | | ABNORMAL | IRREGULAR |
| VARIABLE | | MIDDLE | POSITIVE | | "," |
| | | END | POSITIVE | | "IS-." |

FIG. 4D

| \\ | DOCTOR'S OPINION ELEMENT-TUMEFACTION ||||||
|---|---|---|---|---|---|---|
| \\ | DOCTOR'S OPINION ELEMENT-TUMEFACTION PORTION ||||||
| \\ | DOCTOR'S OPINION ELEMENT-TUMEFACTION DEGREE ||||||
| TYPE | TERM SELECTION BUTTON | USAGE POSITION | USAGE FORMAT | DIFFERENTIATION INFORMATION | EXPRESSION |
| FIXED |  |  |  |  | TUMEFACTION |
| VARIABLE |  | MIDDLE | NEGATIVE |  | "IS NOT PRESENT," |
|  |  | MIDDLE | POSITIVE |  | "IS-," |
|  |  | END | NEGATIVE |  | "IS NOT PRESENT." |
|  |  | END | POSITIVE |  | "IS DOING/DONE." |

FIG. 4E

| TYPE | TERM SELECTION BUTTON | USAGE POSITION | USAGE FORMAT | DIFFERENTIATION INFORMATION | EXPRESSION |
|---|---|---|---|---|---|
| DOCTOR'S OPINION ELEMENT-ATROPHY ||||||
| DOCTOR'S OPINION ELEMENT-ATROPHY PORTION ||||||
| DOCTOR'S OPINION ELEMENT-ATROPHY DEGREE ||||||
| FIXED | | | | | TUMEFACTION |
| VARIABLE | | MIDDLE | NEGATIVE | | "IS NOT PRESENT," |
| | | MIDDLE | POSITIVE | | "IS-," |
| | | END | NEGERTIVE | | "IS NOT PRESENT." |
| | | END | POSITIVE | | "IS DOING/DONE." |

FIG. 4F

| TYPE | TERM SELECTION BUTTON | USAGE POSITION | USAGE FORMAT | DIFFERENTIATION INFORMATION | EXPRESSION |
|---|---|---|---|---|---|
| DOCTOR'S OPINION ELEMENT-SUBSTANCE ||||||
| FIXED | | | | | "SUBSTANCE IS" |
| DOCTOR'S OPINION ELEMENT-SUBSTANCE UNIFORMITY ||||||
| DOCTOR'S OPINION ELEMENT-SUBSTANCE CONCENTRATION ||||||
| VARIABLE | | MIDDLE | POSITIVE | | "," |
| | | END | POSITIVE | | "IS-." |

FIG. 5A

| DOCTOR'S OPINION ELEMENT-TUMEFACTION | |
|---|---|
| DOCTOR'S OPINION ELEMENT-TUMEFACTION PORTION | |
| DOCTOR'S OPINION ELEMENT-TUMEFACTION DEGREE | |
| FIXED | TUMEFACTION |
| VARIABLE | ... |

| DOCTOR'S OPINION ELEMENT-ATROPHY | |
|---|---|
| DOCTOR'S OPINION ELEMENT-ATROPHY PORTION | |
| DOCTOR'S OPINION ELEMENT-ATROPHY DEGREE | |
| FIXED | ATROPHY |
| VARIABLE | ... |

| DOCTOR'S OPINION ELEMENT-SUBSTANCE | |
|---|---|
| FIXED | "SUBSTANCE IS" |
| DOCTOR'S OPINION ELEMENT-SUBSTANCE UNIFORMITY | |
| DOCTOR'S OPINION ELEMENT-SUBSTANCE CONCENTRATION | |
| VARIABLE | ... |

FIG. 5B

| \multicolumn{6}{|c|}{DOCTOR'S OPINION ELEMENT-TUMEFACTION PORTION} |
|---|---|---|---|---|---|
| TYPE | TERM SELECTION BUTTON | USAGE POSITION | USAGE FORMAT | DIFFERENTIATION INFORMATION | EXPRESSION |
| INPUT | ENTIRE LIVER | | | ABNORMAL | "THE ENTIRE LIVER IS" |
| | RIGHT LOBE | | | ABNORMAL | "THE RIGHT LOBE IS" |
| | LEFT LOBE | | | ABNORMAL | "THE LEFT LOBE IS" |

FIG. 5C

| DOCTOR'S OPINION-TUMEFACTION DEGREE | | | | | |
|---|---|---|---|---|---|
| TYPE | TERM SELECTION BUTTON | USAGE POSITION | USAGE FORMAT | DIFFERENTIATION INFORMATION | EXPRESSION |
| INPUT | NON |  | NEGATIVE | NORMAL |  |
|  | LIGHT |  |  | ABNORMAL | LIGHTLY |
|  | MODERATE |  |  | ABNORMAL | MODERATELY |
|  | HIGH |  |  | ABNORMAL | HIGHLY |

FIG. 5D

| \multicolumn{6}{c}{DOCTOR'S OPINION ELEMENT-ATROPHY PORTION} |
|---|---|---|---|---|---|
| TYPE | TERM SELECTION BUTTON | USAGE POSITION | USAGE FORMAT | DIFFERENTIATION INFORMATION | EXPRESSION |
| INPUT | ENTIRE LIVER | | | ABNORMAL | "THE ENTIRE LIVER IS" |
| | RIGHT LOBE | | | ABNORMAL | "THE RIGHT LOBE IS" |
| | LEFT LOBE | | | ABNORMAL | "THE LEFT LOBE IS" |

FIG. 5E

| DOCTOR'S OPINION ELEMENT-ATROPHY DEGREE | | | | | | |
|---|---|---|---|---|---|
| TYPE | TERM SELECTION BUTTON | USAGE POSITION | USAGE FORMAT | DIFFERENTIATION INFORMATION | EXPRESSION |
| INPUT | NON | | NEGATIVE | NORMAL | |
| | LIGHT | | | ABNORMAL | LIGHTLY |
| | MODERATE | | | ABNORMAL | MODERATELY |
| | HIGH | | | ABNORMAL | HIGHLY |

FIG. 5F

| DOCTOR'S OPINION ELEMENT-SUBSTANCE UNIFORMITY | | | | | |
|---|---|---|---|---|---|
| TYPE | TERM SELECTION BUTTON | USAGE POSITION | USAGE FORMAT | DIFFERENTIATION INFORMATION | EXPRESSION |
| INPUT | UNIFORM | | | NORMAL | UNIFORM |
| | NON-UNIFORM | | | ABNORMAL | NON-UNIFORM |
| VARIABLE | | MIDDLE | | | "IS-" |
| | | END | | | |

FIG. 5G

| | DOCTOR'S OPINION ELEMENT-SUBSTANCE CONCENTRATION | | | | |
|---|---|---|---|---|---|
| TYPE | TERM SELECTION BUTTON | USAGE POSITION | USAGE FORMAT | DIFFERENTIATION INFORMATION | EXPRESSION |
| INPUT | LOW | | | ABNORMAL | LOW CONCENTRATION |
| | NORMAL | | | NORMAL | NORMAL CONCENTRATION |
| | HIGH | | | ABNORMAL | HIGH CONCENTRATION |

FIG. 10
| | | |
|---|---|---|
| 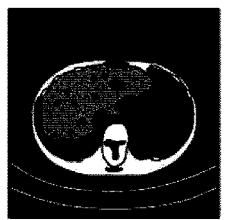 | image1001<br>×× · · · · ××<br>××× | REGISTERED |
| 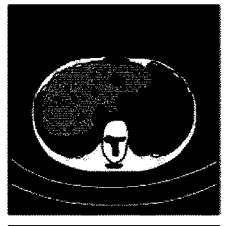 | image25083<br>×× · · · · ××<br>××× | REGISTERED |
| 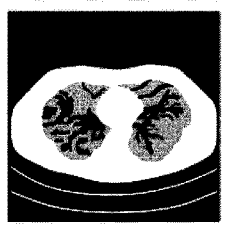 | image37201<br>×× · · · · ××<br>××× | REGISTERED |

MACHINE LEARNING DATA GENERATION SUPPORT APPARATUS, OPERATION METHOD OF MACHINE LEARNING DATA GENERATION SUPPORT APPARATUS, AND MACHINE LEARNING DATA GENERATION SUPPORT PROGRAM

CROSS-REFERENCE TO RELATED APPLICATION

This application claims priority from Japanese Patent Application No. 2017-157672, filed on Aug. 17, 2017, the disclosure of which is incorporated by reference herein in its entirety.

BACKGROUND

Field of the Invention

The present invention relates to a learning data generation support apparatus, a learning data generation support method, and a learning data generation support program that perform support for generating learning data used in machine learning.

Related Art

In the related art, machine learning has been used for learning features of data to perform recognition or classification of images or the like. In recent years, various learning methods have been developed to enhance recognition accuracy. Further, as a processing capability of a computer has been enhanced, a processing time has been reduced. Furthermore, a system has been able to perform deep learning for learning features of image data or the like at a deeper level. By performing the deep learning, it is possible to recognize features of images or the like with extremely high accuracy, and thus, it is expected that discrimination performance is enhanced. A large amount of various data is necessary for the deep learning, and data for discrimination of a large number of images is acquired through the Internet or the like.

On the other hand, in accordance with the spread of a medical information system, for the purpose of cooperation of disease diagnosis and sharing of medical information in districts, realization of a wide range electronic medical record system in which data exchange is possible between medical organizations has been performed. As an elemental technology of a wide range electronic medical record system, there is a medical image management system (PACS: picture archiving and communication system) provided in each medical organization. The PACS performs storage, browsing, and management of image data received from an imaging diagnosis apparatus (modality) such as a computed radiography (CR) apparatus, a computed tomography (CT) apparatus, a magnetic resonance imaging (MRI) apparatus, an ultrasound imaging apparatus, or a positron emission tomography (PET) apparatus. Further, by managing image data using the digital imaging and communication in medicine (DICOM) standard, it is possible to unitarily manage various kinds of image data.

Methods for acquiring a variety of information from a large amount of data that is unitarily managed as mentioned above have been tried. For example, in order to create collective data for each case, a method for retrieving images similar to a certain image or retrieving similar cases on the basis of an interpretation report has been demanded. JP2008-52544A discloses a method for detecting, with respect to one or more pieces of designated image data, image data that is different from the designated image data or is similar thereto, using character information as a retrieval keyword.

In recent years, in a medical field, similarly, methods for recognizing features of images with high accuracy have been demanded for enhancement of diagnosis, and accordingly, usage of deep learning has been reviewed. For the deep learning, learning based on a large amount of high-quality data is essential for its purpose. In the medical field, it may be considered that correct answer data necessary for learning is buried in a large amount of data stored in a medical image management system. However, it is not reasonable to manually discriminate correct answer data from a large amount of data.

For this reason, various methods for automatically detecting correct answer data have been reviewed, but even though a large amount of similar correct answer data is learned, it is possible to obtain uniform performance, and it is difficult to further enhance performance. In reality, by causing data that deviates from a standard in correct answer data to be also learned, it is possible to enhance the entire performance.

SUMMARY

Accordingly, in order to solve the above-described problems, an object of the invention is to provide a learning data generation support apparatus, a learning data generation support method, and a learning data generation support program for generating a variety of learning data necessary for deep learning in a medical field.

According to an aspect of the invention, there is provided a learning data generation support apparatus comprising: retrieval means for analyzing character strings of a plurality of interpretation reports to retrieve an interpretation report in which a retrieval keyword is included; and registration means for performing image processing with respect to a medical image corresponding to the retrieved interpretation report to extract an anatomic region related to the retrieval keyword, and registering information indicating the anatomic region and the medical image as correct answer data in a case where the size of the extracted anatomic region is different from a standard size of the anatomic region or in a case where the shape of the extracted anatomic region is different from a standard shape of the anatomic region.

According to another aspect of the invention, there is provided an operation method of a learning data generation support apparatus that includes retrieval means and registration means, comprising: analyzing character strings of a plurality of interpretation reports to retrieve an interpretation report in which a retrieval keyword is included, using the retrieval means; and performing image processing with respect to a medical image corresponding to the retrieved interpretation report to extract an anatomic region related to the retrieval keyword, and registering information indicating the anatomic region and the medical image as correct answer data in a case where the size of the extracted anatomic region is different from a standard size of the anatomic region or in a case where the shape of the extracted anatomic region is different from a standard shape of the anatomic region, using the registration means.

Further, according to still another aspect of the invention, there is provided a learning data generation support program for causing a computer to function as: retrieval means for analyzing character strings of a plurality of interpretation reports to retrieve an interpretation report in which a retrieval keyword is included; and registration means for performing image processing with respect to a medical image corresponding to the retrieved interpretation report, extracting an anatomic region related to the retrieval keyword, and registering information indicating the anatomic region and the medical image as correct answer data in a case where the size of the extracted anatomic region is different from a standard size of the anatomic region or in a case where the shape of the extracted anatomic region is different from a standard shape of the anatomic region.

The "anatomic region" refers to an organ region or a lesion region.

The "size of the anatomic region is different from a standard size of the anatomic region" means that the size of the anatomic region is a size that deviates from a range of the standard size of the anatomic region, and "the shape of the anatomic region is different from a standard shape of the anatomic region" means that the shape of the anatomic region is a shape that deviates from a range of the standard shape of the anatomic region. Further, the range of the standard size or the range of the standard shape of the anatomic region is determined using an index determined in accordance with a feature of the anatomic region, for example, which means a range in which an index value has a determined width from a predetermined reference value. The standard size of the anatomic region may be determined using a value of the length of the anatomic region in the long axis direction, for example, and the standard shape of the anatomic region may be determined using a value of circularity, for example.

The "interpretation report in which a retrieval keyword is included" not only may be an interpretation report in which a retrieval keyword is included as it is, but also may be an interpretation report in which content capable of being determined to be substantially the same as the retrieval keyword is included. For example, a different term indicating the same target may be considered to be the same as the retrieval keyword, and a term having a different arrangement order but having the same content may be considered to be the same as the retrieval keyword. Further, a term capable of being determined to have the same content according to a predetermined rule, as in an obscure retrieval, may be considered to be the same as the retrieval keyword.

Further, the registration means may determine whether or not the size of the extracted anatomic region is different from the standard size of the anatomic region on the basis of the size of an anatomic region of a medical image that is set as a reference image in advance, or determine whether or not the shape of the extracted anatomic region is different from the standard shape of the anatomic region on the basis of the shape of an anatomic region of a medical image that is set as a reference image in advance.

Further, the retrieval means may execute natural language analysis with respect to the interpretation report to extract information relating to the size or shape of the anatomic region.

The retrieval keyword may include a character string that means a change of a state of the anatomic region that is present in two or more medical images obtained by imaging the same patient at different times.

The retrieval keyword may be a character string indicating a state of a cancer.

The anatomic region may be any one of the lung, the liver, the kidneys, the heart, and the large intestine.

The anatomic region may be a region of the cancer.

The retrieval keyword may include the kind of the cancer.

Further, the medical image may be an MRI image, a CT image, a simple X-ray image, or an ultrasound image.

Further, input reception means for receiving an input of the retrieval keyword may be further included, and the retrieval means may retrieve the interpretation report in which the input retrieval keyword is included.

According to the invention, by analyzing character strings of a plurality of interpretation reports to retrieve an interpretation report in which a retrieval keyword is included, and registering, in a case where the size of an anatomic region of a medical image corresponding to the retrieved interpretation report is different from a standard size of the anatomic region or in a case where the shape of the extracted anatomic region is different from a standard shape of the anatomic region, information indicating the anatomic region and the medical image as correct answer data, it is possible to automatically acquire a variety of correct answer data necessary for deep learning.

BRIEF DESCRIPTION OF THE DRAWINGS

FIG. 3 is a diagram showing an example of a report editing screen.

FIGS. 4A-4F are diagrams showing a first exemplary dictionary table.

FIGS. 5A-5G are diagrams showing a second exemplary dictionary table.

FIG. 10 is a diagram showing an example of a list of correct answer data.

DETAILED DESCRIPTION

Figure 1:
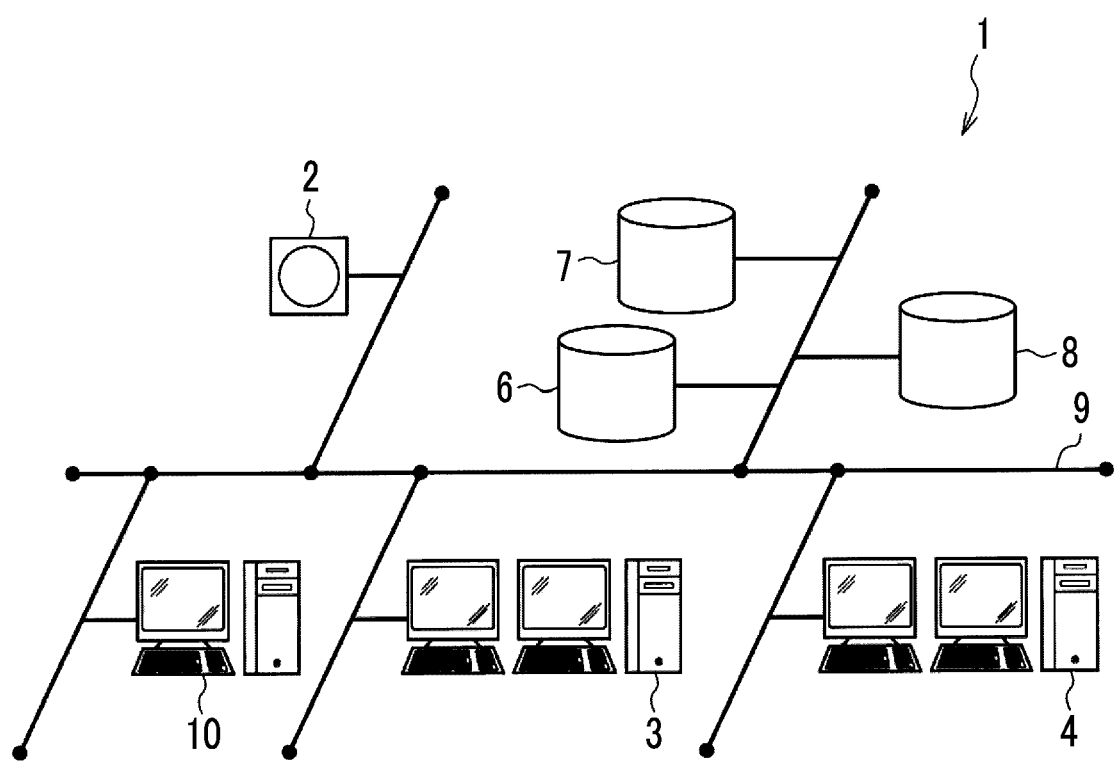
FIG. 1 is a diagram showing a schematic configuration of a medical information system.

FIG. 1 shows a schematic configuration of a medical information system 1 in which a learning data generation support apparatus according to a first embodiment of the invention is introduced. The medical information system 1 is a system for performing imaging and storage of an inspection target portion of a subject, interpretation of a captured image and creation of an interpretation report from a radiologist in a radiology department, and browsing of the interpretation report and detailed observation of an image that is an interpretation target from a doctor in a diagnosis and treatment department that is a client, on the basis of an inspection order given from the doctor in the diagnosis and treatment department using a known ordering system. As shown in FIG. 1, the medical information system 1 is configured so that an imaging apparatus (hereinafter, referred to as a modality) 2, a radiologist workstation 3, a diagnosis and treatment department workstation 4, an electronic medical record database 6, an image database 7, and an interpretation report database 8 are connected to each other in a communicable state through a network 9. In each device, an application program for causing the device to function as a component of the medical information system 1 is installed. Further, the application program may be installed from a recording medium such as a CD-ROM, or may be installed after being downloaded from a storage of a server connected through a network such as the Internet.

The modality 2 includes a device that images an inspection target portion of a subject to generate an inspection image that represents the inspection target portion, and adds accessory information (hereinafter, referred to as a DICOM tag) regulated in the DICOM standard to the inspection image for output. As a specific example, a CT apparatus, an MRI apparatus, an ultrasound imaging apparatus, a CR apparatus, or the like may be used.

The radiologist workstation 3 is a computer that is used by a radiologist for interpretation of an image or creation of an interpretation report in a radiology department, and includes a known hardware configuration such as a central processing unit (CPU), a main memory, an auxiliary storage, an input/output interface, a communication interface, an input device, a display device, a data bus, and the like. Further, in the radiologist workstation 3, a known operation system or the like is installed. As the display device, one or plural high definition displays are provided. In the radiologist workstation 3, respective processes such as transmission request of an image with respect to the image database 7, display of an image received from the image database 7, creation support and display of an interpretation report, automatic detection and highlighting of a lesion likeliness portion in an image, and the like are performed by executing a software program for the respective processes. Further, the radiologist workstation 3 transmits a generated interpretation report to the interpretation report database 8 through the network 9, and requests registration thereof.

The diagnosis and treatment department workstation 4 is a computer that is used by a doctor in a diagnosis and treatment department for browsing and input of an electronic medical record, issuing of an inspection order, detailed observation of an image, browsing of an interpretation report, and the like, and includes a known hardware configuration such as a CPU, a main memory, an auxiliary storage, an input/output interface, a communication interface, an input device, a display device, a data bus, and the like. Further, in the diagnosis and treatment department workstation 4, a known operation system or the like is installed. As the display device, one or plural high definition displays are provided.

In the diagnosis and treatment department workstation 4, operating instructions such as an instruction for input and editing of a medical record and an instruction for input and issuing of an inspection order are input through the input device (a keyboard, a mouse, or the like). Data on the input medical record or inspection order is registered in the electronic medical record database 6 through the network 9.

Further, in the diagnosis and treatment department workstation 4, respective processes such as browsing request of an image with respect to the image management server 5, display of an image received from the image management server 5, automatic detection and highlighting of a lesion likeliness portion in an image, browsing request of an interpretation report with respect to the interpretation report database 8, display of an interpretation report received from the interpretation report database 8, and the like are performed by executing a software program for the respective processes. Further, the diagnosis and treatment department workstation 4 transmits an image obtained by ultrasound diagnosis or the like performed in each diagnosis and treatment department to the image management server 5 through the network 9, and requests registration of the image into the image database 7.

The electronic medical record database 6 has a configuration in which a software program for providing a function of a database management system (DBMS) is installed in a general-purpose computer. The electronic medical record database 6 is provided with a large capacity storage. The storage may be a large capacity hard disk drive connected through a data bus, or may be a disk device connected to a network attached storage (NAS) or a storage area network (SAN) connected to the network 9.

In the electronic medical record database 6, electronic medical records of a plurality of patients on which information obtained by doctor's questions or the like is recorded are stored in association with patient information such as patient IDs, patient names, ages, or genders.

The image database 7 has a configuration in which a software program for providing a function of a database management system is installed in a general-purpose computer. The image database 7 is provided with a large capacity storage. The storage may be a large capacity hard disk drive connected through a data bus, or may be a disk device connected to the NAS or the SAN connected to the network 9.

In the image database 7, inspection images obtained by imaging a plurality of patients using the modality 2 and accessory information are registered. The accessory information includes information such as an image identification (ID) for identifying each image, a patient ID for identifying a subject, an inspection ID for identifying inspection, a unique identification (UID) allocated to each inspection image, an inspection date on which an inspection image is generated, an inspection time point, the type of a modality used in inspection for acquiring the inspection image, an inspection portion (imaging portion), an imaging condition (the presence or absence of usage of a contrast medium, a radiation dose, or the like), and serial numbers or the like in acquiring a plurality of tomographic images in one inspection.

Further, in a case where a browsing request is received from the radiologist workstation 3 through the network 9, the image database 7 retrieves an inspection image registered in the above-described image database 7, and transmits the extracted inspection image to the radiologist workstation 3 that is a request source.

The interpretation report database 8 has a configuration in which a software program that provides a function of a database management system (DBMS) is installed in a general-purpose computer. In a case where a registration request of an interpretation report is received from the radiologist workstation 3, the interpretation report is registered in the interpretation report database 8 in accordance with a database format.

In the interpretation report database 8, an interpretation report in which information such as an image ID for identifying an interpretation target image or a representative image, a radiologist ID for identifying an image diagnosis doctor who performs interpretation, a lesion name, lesion position information, a doctor's opinion and the degree of conviction of the doctor's opinion is recorded is registered. Further, in the interpretation report, a determination result obtained through a biopsy is recorded.

The network 9 is a local area network through which various devices in a hospital are connected to each other. In a case where the radiologist workstation 3 is provided in another hospital or clinic, the network 9 may be configured to connect local area networks in respective hospitals through the Internet or an exclusive line. In any case, it is preferable that the network 9 has a configuration capable of realizing high-speed transmission of an inspection image, such as an optical network or the like.

Figure 2:
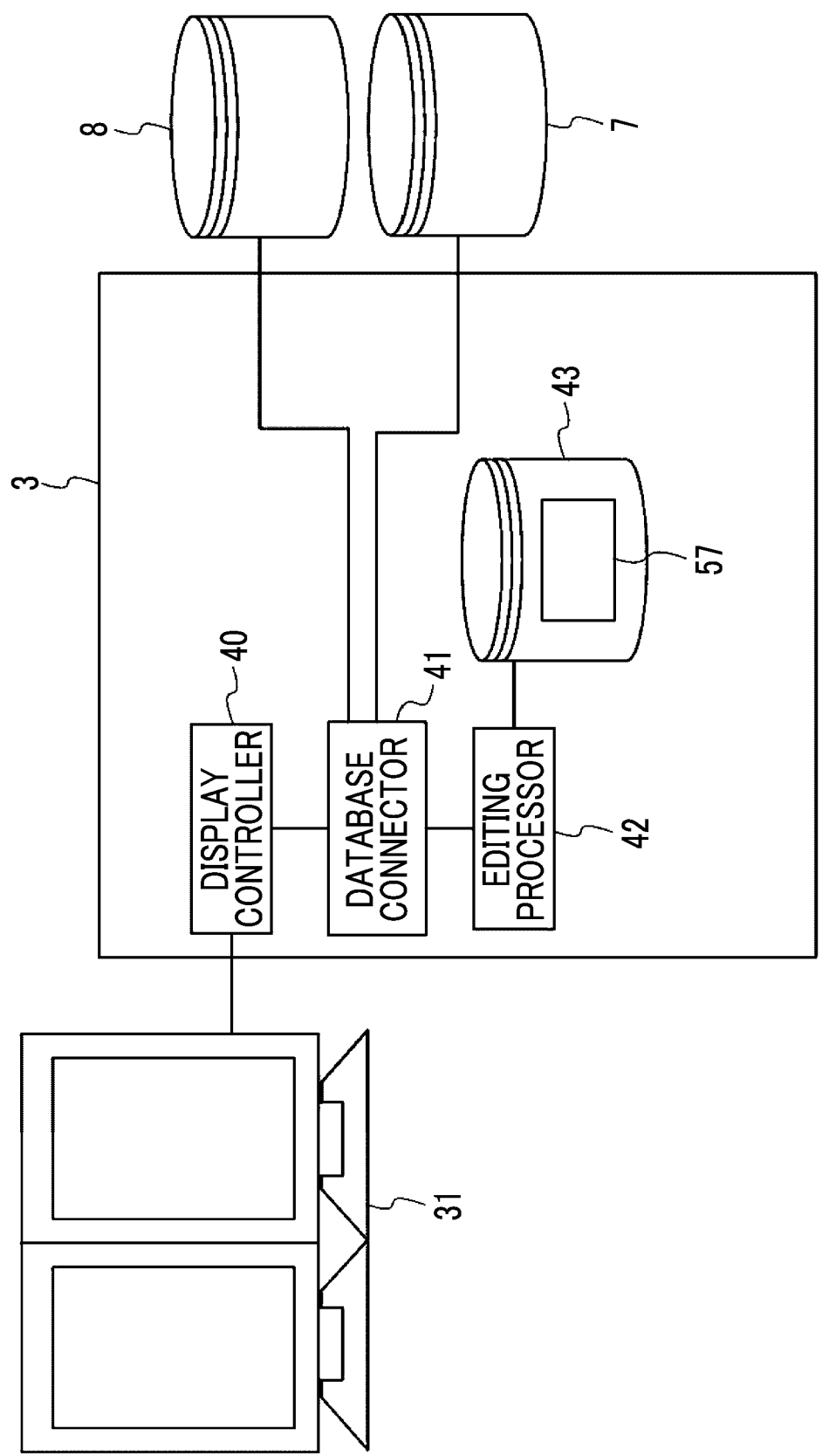
FIG. 2 is a diagram showing a schematic configuration of a radiologist workstation.

Next, functions of the radiologist workstation 3 will be described. As shown in FIG. 2, the radiologist workstation 3 includes display control means (display controller) 40, database connection means (database connector) 41, editing processing means 42 (editing processor) 42, and storage means (storage) 43.

The database connector 41 performs data transmission and reception with respect to the image database 7 and the interpretation report database 8 through the network 9.

The display controller 40 has a function of controlling display of a display 31 connected to the radiologist workstation 3, and has a function of causing the display 31 to display an inspection image received from the image database 7 and causing the display 31 to display an input screen of an interpretation report.

Functions of the display controller 40 will be described in detail with reference to FIGS. 3 to 5. FIGS. 3 to 5 are examples of display screens in a case where an interpretation report is input from a radiologist workstation. Here, a case where two displays 31 are connected to the radiologist workstation 3 will be described.

The display controller 40 displays various inspection images (corresponding to medical images) such as a simple X-ray image based on radiation imaged by a CR apparatus, a tomographic image captured by a CT apparatus or an MRI apparatus, a three-dimensional image generated on the basis of a tomographic image on a display screen of one display 31. A plurality of inspection images may be simultaneously displayed on the display screen.

Further, the display controller 40 displays a report editing screen 44 shown in FIG. 3 on a display screen of the other display 31. Various operating tools that form a graphical user interface (GUI), such as an operating button, a list box, or an icon, are provided on the report editing screen 44. Various operating instructions are input through the input device using the above-mentioned operating tools.

A basic information display region 45, a doctor's opinion sentence input region 46, a term selection input region 47, and an operating button region 48 are provided on the report editing screen 44. The respective regions correspond to the various operating tools that form the GUI. Various operating instructions are input through the input device using the above-mentioned operating tools. The operating instructions include an instruction for reading out data of an interpretation report from the interpretation report database 8, an instruction for storing data of an interpretation report in the interpretation report database 8, an instruction for selecting the doctor's opinion sentence input region 46 for activation (into a state where input is possible), and the like.

In the basic information display region 45, basic information such as a patient name ("Fuji Ichiro"), an inspection ID ("CT0803"), an inspection image capturing date ("08/4/12 (Apr. 12, 2008)" is displayed.

An observation record relating to a lesion state or the like, obtained by observing and recognizing an inspection image from a radiologist, that is, a sentence indicating a doctor's opinion (hereinafter, referred to as a doctor's opinion sentence) is input to the doctor's opinion sentence input region 46. In FIG. 3, only one doctor's opinion sentence input region 46 is displayed, but another doctor's opinion sentence input region 46 may be added thereto. A case where another doctor's opinion sentence input region 46 is added thereto may be a case where a plurality of lesions are present and a doctor's opinion is dividedly input for each lesion, or may be a case where a plurality of inspection objects are present (for example, therapeutic effect determination, metastasis retrieval, and the like) and a doctor's opinion is dividedly input for each inspection object.

In the term selection input region 47, operating tools (which may be referred to as template-type operating tools) for inputting a doctor's opinion sentence to the doctor's opinion sentence input region 46 through a mouse click operation are displayed. The term selection input region 47 has large classification panels 49 for organs such as the "liver", "bile ducts", or the "gall bladder", and small classification panels 50. The small classification panels 50 have doctor's opinion items. Here, items to be written as doctor's opinions for each organ, such as the "type of the liver" or a "tumor lesion", are classified. The panels 49 and 50 may be selectively switched by a tab, respectively. An organ name selected as the large classification panel 49 is displayed beside the doctor's opinion sentence input region 46. In this example, the "liver" is selected as the large classification panel 49, and the "type of the liver" is selected as the small classification panel 50, respectively.

A plurality of term selection buttons 51 are provided in the small classification panels 50. The term selection buttons 51 are horizontally arranged for each doctor's opinion element such as a "margin", a "surface", the "degree of tumefaction", or a "tumefaction portion" for subdividing the doctor's opinion items. For example, the doctor's opinion element of the "margin" includes "sharp", "slightly dull", and "dull", and the doctor's opinion element of the "surface" includes "smooth", "slightly irregular", and "irregular". As the terms of the term selection buttons 51, medical terms that are highly frequently used in each doctor's opinion element are used.

With respect to each doctor's opinion element, only one term selection button 51 is selectable. Accordingly, for example, in a state where the "margin-sharp" is selected, in a case where the "margin-dull" is re-selected, the selection of the "margin-sharp" is automatically released.

In a state where the doctor's opinion sentence input region 46 is activated, in a case where a pointer 52 is pointed to a desired term selection button 51 and a click operation is performed using a mouse, a doctor's opinion sentence based on a selected term is displayed in the doctor's opinion sentence input region 46. The doctor's opinion sentence input to the doctor's opinion sentence input region 46 may be modified or revised by operating a keyboard.

The doctor's opinion sentence is displayed when one or more term selection buttons 51 are selected. The display of the doctor's opinion sentence is updated whenever the term selection button 51 is additionally selected. The additional selection includes a case where term selection buttons 51 of two doctor's opinion elements are selected, and then, a term selection button 51 of a third doctor's opinion element is selected, and a case where the term selection button 51 is re-selected in the same doctor's opinion element.

In this example, as the term selection buttons 51, "margin-sharp", "surface-smooth", the "degree of tumefaction-light", "tumefaction portion-left lobe", the "degree of atrophy-non", "substance uniformity-uniform", and "substance concentration-normal" are respectively selected (indicated by oblique lines), and only "Atrophy portion" is not selected. Further, a state where "The left lobe of the liver is lightly tumefacient. The margin is sharp, the surface is smooth, and no atrophy is shown. The substance is uniform, and the concentration is normal." is displayed as the doctor's opinion sentence in the doctor's opinion sentence input region 46 is shown.

Data on the doctor's opinion sentence (hereinafter, referred to as doctor's opinion sentence data) input to the doctor's opinion sentence input region 46 is given a doctor's opinion ID for identifying an individual doctor's opinion sentence. The doctor's opinion ID is used for association of an inspection image or an interpretation report and a doctor's opinion sentence, and includes a number that is assigned in an order in which the doctor's opinion sentence is added to the doctor's opinion sentence input region 46.

In a case where an end button 54 is selected, data on an interpretation report is confirmed and stored. In order to prevent unauthorized falsification, editing of the confirmed and stored interpretation report is prohibited.

The editing processor 42 receives a doctor's opinion data input to the doctor's opinion sentence input region 46 of the report editing screen 44 and selections of the respective panels 49 and 50, and the term selection buttons 51.

The editing processor 42 adds, with respect to each doctor's opinion data, a doctor's ID for identifying a radiologist who inputs the doctor's opinion sentence, in addition to the doctor's opinion ID. The doctor ID is input by the radiologist in user authentication in a case where the radiologist workstation 3 is started, for example.

Further, the editing processor 42 creates a doctor's opinion sentence based on selection states of the respective panels 49 and 50, and the term selection buttons 51, on the basis of a dictionary table 57 stored in the storage 43.

On the left side in FIG. 4, the dictionary table 57 has a hierarchical structure in which items of organs are disposed in the highest layer and the doctor's opinion items and doctor's opinion elements are sequentially disposed in lower layers. The organs and the doctor's opinion items, and the doctor's opinion items and the doctor's opinion elements are respectively disposed in different layers, and the respective organs, the respective doctor's opinion items, and the respective doctor's opinion elements are disposed in the same layers. The "liver", the "bile ducts", and the like of the large classification panels 49 are registered in the items of the organs, the "type of the liver", the "tumor lesion", and the like of the small classification panels 50 are registered in the doctor's opinion items, and the "margin", the "surface", the "degree of tumefaction", the "tumefaction portion", and the like are registered in the doctor's opinion elements, respectively. In lower layers of the "tumefaction", "atrophy", and "substance" that are the doctor's opinion elements, doctor's opinion elements of the "tumefaction portion", the "degree of tumefaction", the "Atrophy portion", the "degree of atrophy", "substance uniformity", and "substance concentration" are connected, respectively. Although not shown, the "bile ducts" and the "gall bladder" that are the items of the organs, the "tumor lesion" and the like that are the doctor's opinion items also have a plurality of doctor's opinion items and doctor's opinion elements in lower layers, respectively.

On the right side of FIG. 4, and in FIG. 5, in each doctor's opinion element, expressions that form a clause relating to a doctor's opinion elements are registered. The expressions have three types of fixed, input, and variable. Among the doctor's opinion elements, there is a doctor's opinion element in which the entire types of expressions are registered, and there is a doctor's opinion element in which any one of the types of expressions is registered.

The fixed expressions include "margin", "surface", "tumefaction", and the like, which are the same as the doctor's opinion elements. Each fixed expression should be included in a doctor's opinion sentence in a case where a term selection button 51 that belongs to a corresponding doctor's opinion element is selected.

The input expressions include "sharp", "dull", "slightly irregular", and the like, which are the same as displays of the terms of the term selection buttons 51 except that the input expressions such as the doctor's opinion element of "substance concentration" or the like are slightly different from the displays of the terms of the term selection buttons 51. Each input expression should be included in the doctor's opinion sentence in a case where a corresponding term selection button 51 is selected, except that "tumefaction-non" and "atrophy-non" are selected.

In the input expressions, differentiation information is defined as attributes. The differentiation information has two types of "normal" and "abnormal". In a case where an input expression is a medical term indicating a normal state from a medical viewpoint, the differentiation information becomes "normal", and in a case where the input expression is a medical term indicating an abnormal state, the differentiation information becomes "abnormal". The input expressions of which the differentiation information is "normal" have six expressions, that is, "margin-sharp", "surface-smooth", the "degree of tumefaction-non", the "degree of atrophy-non", "substance uniformity-uniform", "substance concentration-normal" in this example, and all the other input expressions are defined as "abnormal".

The variable expressions include ",", "is not present,", "is doing/done.", or the like, which are variable according to selection states of the term selection buttons 51. In the variable expressions, usage positions and usage formats are defined as attributes. The usage positions have two types of the "middle" and the "end", and the usage formats have two types of "positive" and "negative", respectively. A variable expression (",", "is not present,", or the like) of which the usage position is the "middle" is used in a case where a clause relating to a corresponding doctor's opinion element is a clause in the middle of a doctor's opinion sentence. A variable expression ("is doing/done.", or the like) of which the usage position is the "end" is used in a case where a clause relating to a corresponding doctor's opinion element is a clause at the end of a doctor's opinion sentence.

A variable expression ("do-,", "is doing/done.", or the like) of which the usage format is "positive" is used in a case where a clause relating to a corresponding doctor's opinion element is a positive form. A variable expression ("is not present,", "is not present.", or the like) of which the usage format is "negative" is used in a case where a clause relating to a corresponding doctor's opinion element is a negative form. In this example, a case where the clause relating to the corresponding doctor's opinion element is the negative form means a case where "non" is selected by the term selection button 51 in the doctor's opinion elements of the "degree of tumefaction" and the "degree of atrophy". The other cases are cases indicating "positive".

In a case where any one of the term selection buttons 51 is selected, the editing processor 42 first traces a hierarchy of items of organs, and doctor's opinion items in the dictionary table 57, corresponding to selection states of the respective panels 49 and 50. Further, the editing processor 42 reads out fixed expressions and input expressions of doctor's opinion elements (hereinafter, referred to as doctor's active opinion elements) corresponding to the selected term selection buttons 51 from the dictionary table 57. In a case where doctor's opinion elements in a lower layer (child), that is, the term selection buttons 51 of the "degree of tumefaction", the "tumefaction portion", the "degree of atrophy", the "Atrophy portion", the "substance uniformity", and the "substance concentration" in this example are selected, the "tumefaction", the "atrophy", and the "substance" that are doctor's opinion elements in an upper layer (parent) also become automatically active, and the expressions of the doctor's opinion elements in the upper layer are also automatically read out to the editing processor 42.

The editing processor 42 acquires differentiation information of the input expressions read out from the dictionary table 57. In a case where the differentiation information of all the read-out input expressions is normal or abnormal, the editing processor 42 does not perform switching between clauses to be described hereinafter.

In a case where the differentiation information of the input expressions read out from the dictionary table 57 is a mixture of normal and abnormal, the editing processor 42 picks up an input expression of which the differentiation information is abnormal. Then, the editing processor 42 allocates a clause (hereinafter, referred to as a second clause) relating to a doctor's opinion element in which the input expression of which the differentiation information is abnormal is selected at the head of a doctor's opinion sentence and allocates a clause (hereinafter, referred to as a first clause) relating to a doctor's opinion element in which the input expression of which the differentiation information is normal is selected at the back. In a case where a clause (in this example, "margin") relating to a doctor's opinion element of which a registration order in the dictionary table 57 is first is the second clause, reclassification of the clause is not performed.

Subsequently, the editing processor 42 determines a variable expression of the doctor's active opinion element. The editing processor 42 checks a usage position and a usage format of a clause relating to the doctor's active opinion element. The editing processor 42 checks whether a doctor's opinion element that is at the same hierarchical level as that of the doctor's active opinion element is active in the registration order in the dictionary table 57. In a case where the differentiation information of all the input expressions read out from the dictionary table 57 is normal or abnormal and a different doctor's active opinion element is present behind the doctor's active opinion element that is a determination target of the usage position and the usage format, the usage position is the middle. In other cases, the usage position becomes the end.

In a case where the differentiation information of the input expressions read out from the dictionary table 57 is mixture of normal and abnormal, a usage position of the second clause that is at a boundary with respect to the first clause among the second clauses allocated at the head of the doctor's opinion sentence becomes the "end". A usage position of the other second clause becomes the "middle". Similarly, a usage position of the first clause that is allocated at the back is set in the same way as in a case where the differentiation information of all the input expressions read out from the dictionary table 57 is normal or abnormal. Briefly speaking, the editing processor 42 distinguishes between the first clause and the second clause, sets the position of the second clause in a front portion of a doctor's opinion sentence, puts a punctuation mark thereafter, and then, disposes the first clause behind the second clause.

In a case where the usage formats of the input expressions corresponding to the selected term selection buttons 51 are "negative", that is, in a case where the "degree of tumefaction-non" and the "degree of atrophy-non" in this example are selected, the editing processor 42 determines that the usage formats of the "degree of tumefaction" that is a doctor's active opinion element and the "tumefaction" in the upper layer thereof, and the "degree of atrophy" and the "atrophy" in the upper layer thereof are "negative". The other cases are determined to be cases indicating "positive". As obvious from the above description, the usage formats of the doctor's opinion elements in the lower layer are also applied to the doctor's opinion elements in the upper layer thereof. As described above, the editing processor 42 connects various expressions read out from the dictionary table 57 in the arrangement (registration) order in the dictionary table 57 to create a doctor's opinion sentence.

A creation process of a doctor's opinion sentence in the editing processor 42 will be described with reference to selection states of the respective panels 49 and 50, and the term selection buttons 51 in FIG. 3. Since the "liver" and the "shape of the liver" are selected as the respective panels 49 and 50, the editing processor 42 traces the "liver" and the "shape of the liver" in the lower layer thereof in the dictionary table 57. Further, the editing processor 42 reads out the "margin", the "tumefaction", the "substance", and the like that are the fixed expressions of the doctor's active opinion elements (in this case, all of the "margin" to "substance"), and the "sharp", the "lightly", the "left lobe is", the "normal concentration", and the like that are the input expressions from the dictionary table 57.

In this case, abnormal doctor's opinion elements are the "tumefaction portion" and the "degree of tumefaction", and all the other doctor's opinion elements are normal. Thus, "The left lobe of the liver is lightly tumefacient." that is a clause relating to the doctor's opinion element "tumefaction" that is the second clause is allocated at the head of a doctor's opinion sentence, and the other first clauses "the margin is sharp, the surface is smooth, . . . " are allocated at the back. Further, as the clause relating to the doctor's opinion element "tumefaction", the variable expression "is doing/done." of which the usage position is the "end" is selected. In the clauses relating to the other doctor's opinion elements, the usage positions are "the middle" with respect to the doctor's opinion elements from the "margin" to the "substance uniformity". Further, since the "degree of atrophy-non" is selected, the usage format of the doctor's opinion element "atrophy" is negative, and in all the other cases, the usage formats are "positive". Accordingly, the editing processor 42 selectively reads out ",", "is not present,", "is-,", and "is-." as the variable expressions from the dictionary table 57. The various expressions read out in this way are connected to each other according to a predetermined order to form a doctor's opinion sentence.

As another example, in a case where only the "margin-dull" is selected, a doctor's opinion sentence of "The margin is dull." is obtained. Further, in a case where only the "degree of tumefaction-non" is selected, a doctor's opinion sentence of "The tumefaction is not present." is obtained. In a case where the "degree of atrophy-moderate" and the "Atrophy portion-entire liver" are only selected, a doctor's opinion sentence of "The entire liver is moderately atrophied." is obtained. In a case where only the "substance-not uniform" is selected, a doctor's opinion sentence of "The substance is not uniform." is obtained.

In a case where the "margin-dull" and the "surface-smooth" are selected, since the differentiation information of "dull" is abnormal and the "smooth" is normal, a doctor's opinion sentence of "The margin is dull. The surface is smooth." is obtained. In a case where the "margin-sharp", the "surface-irregular", the "degree of atrophy-significant", and the "Atrophy portion-left lobe" are selected, a doctor's opinion sentence of "The surface is irregular, and the left lobe is significantly atrophied. The margin is sharp." is obtained. In a case where there is one doctor's active opinion element, a doctor's opinion sentence becomes a short sentence, and in a case where there are a plurality of doctor's active opinion elements, a doctor's opinion sentence becomes a compound sentence that includes clauses relating to respective doctor's opinion elements. In a case where the differentiation information of input expressions read out from the dictionary table 57 is a mixture of normal and abnormal, a doctor's opinion sentence includes the second clause at the head and the first clause subsequent thereto.

The arrangement (registration) order of doctor's opinion elements corresponds to positions of clauses relating to the respective doctor's opinion elements in a doctor's opinion sentence. That is, in a case where the differentiation information of all input expressions read out from the dictionary table 57 is normal or abnormal and all the doctor's opinion elements are active, a clause relating to a doctor's opinion element of the "margin" is allocated at the head of a doctor's opinion sentence, and clauses relating to the "surface", the "tumefaction", and the like are subsequent thereto in the order. Further, a clause relating to the "substance" is positioned at the end of the doctor's opinion sentence. With respect to clauses relating to the doctor's opinion elements "tumefaction", "atrophy", and "substance" in which the doctor's opinion elements are connected in the lower layer, the arrangement order of the doctor's opinion elements in the lower layer is reflected in the doctor's opinion sentence. For example, clauses relating to the doctor's opinion element "tumefaction" are combined in the order of the "tumefaction portion" and the "degree of tumefaction". In a case where the differentiation information of input expressions read out from the dictionary table 57 is a mixture of normal and abnormal, a doctor's opinion sentence is created so that positions are set in accordance with the arrangement order of the doctor's opinion elements in each of the first and second clauses.

Further, an arrangement (registration) order of respective expressions of each doctor's opinion element also corresponds to positions of expressions in a clause relating to the doctor's opinion element. For example, in a clause relating to the doctor's opinion element "margin", the fixed expression "margin" comes at the head, and thereafter, an input expression and a variable expression are disposed. In a clause relating to the doctor's opinion element "substance", the fixed expression "The substance is" comes at the head, and thereafter, an input expression and a variable expression of the doctor's opinion element "substance uniformity" are disposed. Thereafter, an input expression of the doctor's opinion element "substance concentration" is disposed. Further, finally, a variable expression of the doctor's opinion element "substance" is disposed.

Since the doctor's opinion element "substance" forms a clause that comes at the end of a doctor's opinion sentence, it is preferable that a variable expression is not registered and the end of the doctor's opinion element "substance concentration" is set as "is-.", but in addition to "is-." of which the usage position is the end, "," of which the usage position is the middle is also registered. In this example, since the clause of the doctor's opinion element "substance" is not disposed in the middle, "," is not used, but in a case where a new doctor's opinion element is additionally registered behind the doctor's opinion element "substance", the clause of the doctor's opinion element "substance" may be disposed in the middle. Accordingly, in consideration of a case where the new doctor's opinion element is additionally registered, "is-." and "," are registered. For the same reason, the end of the variable expression of the doctor's opinion element "substance uniformity" is remained to be empty. With respect to other doctor's opinion elements, similarly, in consideration of a case where a new doctor's opinion element or expression is additionally registered, it is preferable to form definitions or an arrangement order in order to avoid waste, for example, to define a usage format even with respect to an input expression.

Here, with respect to clauses relating to the doctor's opinion elements "tumefaction" and "atrophy", description of either of a meaning that the tumefaction or the atrophy is present to a certain degree (light, moderate or significant) in a certain portion (the entire liver, the right lobe, or the left lobe) and the tumefaction or the atrophy is not present in portions other than the selected portion or a meaning that the tumefaction or the atrophy is not present in any portion of the liver is assumed.

Figure 6:
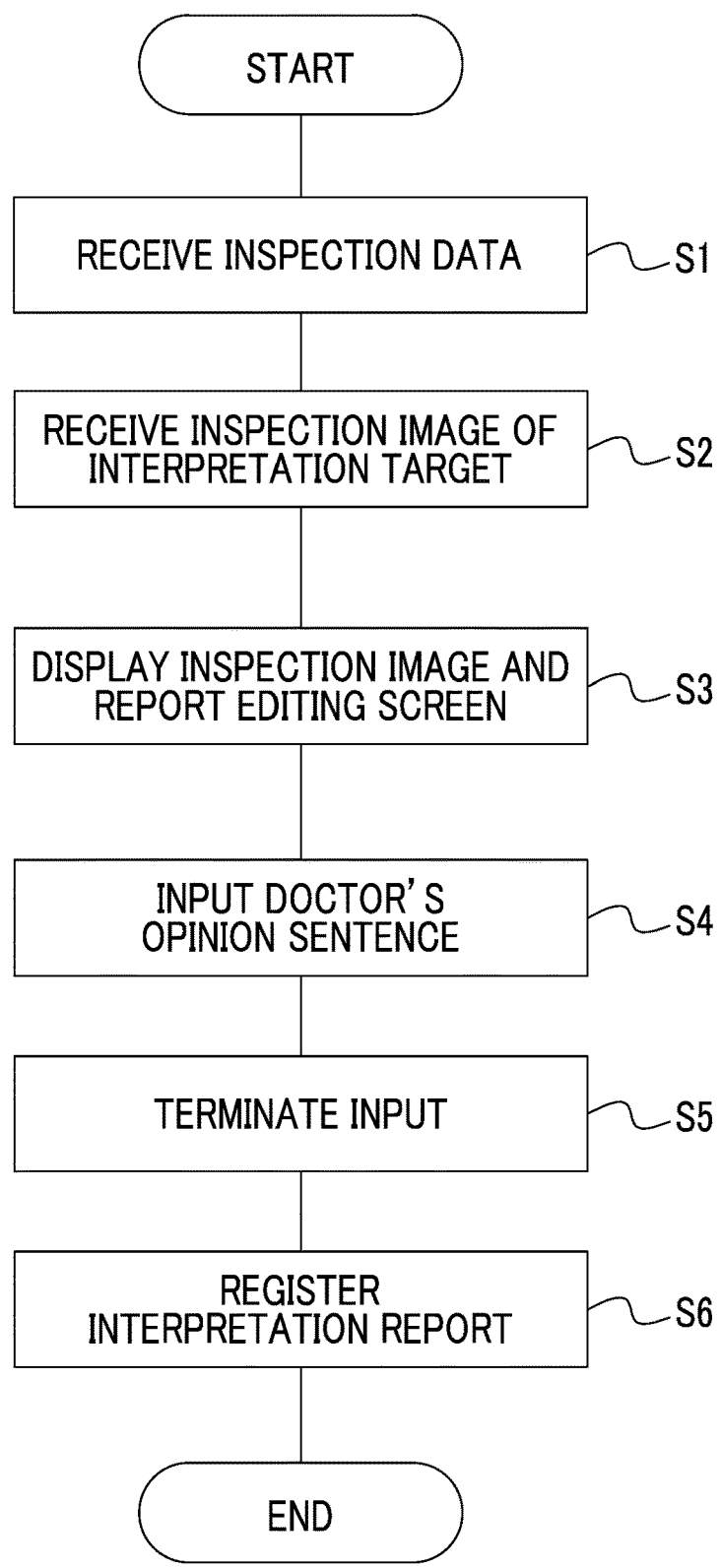
FIG. 6 is a flowchart showing a flow of a process of creating an interpretation report in the radiologist workstation.

Hereinafter, a flow of processes of the radiologist workstation 3 based on the above-mentioned configuration will be described with reference to a flowchart shown in FIG. 6.

The radiologist workstation 3 receives an inspection order issued from the diagnosis and treatment department workstation 4 (S1). A radiologist confirms the inspection order in the radiologist workstation 3, and starts creation of an interpretation report. The radiologist requests an inspection image corresponding to the inspection order from the image database 7 through the database connector 41, and receives an inspection image that is an interpretation target (S2). The display controller 40 displays the report editing screen 44 on a second display, and displays the inspection image on a first display in conjunction therewith (S3). The radiologist inputs a doctor's opinion sentences for each organ in the doctor's opinion sentence input region 46 of the report editing screen 44 of the second display while observing the inspection image (S4).

The input of the doctor's opinion sentence is performed by selecting the term selection buttons 51 as described above. The created doctor's opinion sentence is displayed in the doctor's opinion sentence input region 46 by the editing processor 42. In this way, the radiologist inputs the doctor's opinion sentence while selecting the term selection buttons 51.

After finishing the input of the doctor's opinion sentence, the radiologist selects the end button 54 (S5). Data of the interpretation report is transmitted to the interpretation report database 8 from the database connector 41, and then, registration is performed (S6).

In the above description, the liver has been described as an example, but it is possible to prepare a dictionary table based on respective organs and to input doctor's opinion sentences while selecting terms.

Next, the learning data generation support apparatus 10 according to the first embodiment of the invention will be described in detail.

The learning data generation support apparatus 10 of the invention is connected to the network 9, and is connected to the image database 7 and the interpretation report database 8 through the network 9 (see FIG. 1).

The learning data generation support apparatus 10 is configured of a general-purpose computer, and includes a known hardware configuration such as a CPU, a main memory, an auxiliary storage, an input/output interface, a communication interface, an input device, a display device, a data bus, and the like. In learning data generation support apparatus 10, a known operation system, an application program, or the like is installed, and a learning data generation support program of the invention is also installed. Further, the learning data generation support apparatus 10 performs transmission and reception of data with respect to the image database 7 and the interpretation report database 8 connected to the network 9 through a communication interface. The learning data generation support program may be installed from a recording medium such as a compact disc read only memory (CD-ROM), or may be installed through a network such as the Internet.

It is assumed that a medical image stored in the image database 7 includes an image in which information indicating a correct anatomic region created by a doctor is stored. As the information indicating the anatomic region, for example, a mask image obtained by masking a range when an anatomic region (for example, an organ region or a lesion region) is correctly recognized on a medical image may be used. Alternatively, data in which position information indicating a range of an anatomic region is stored may be used. Hereinafter, in this embodiment, a case where a medical image suitable for correct answer data is retrieved from medical images having information indicating a correct anatomic region will be described. Further, a case where the information indicating the correct anatomic region is a mask image will be described hereinafter as an example.

Figure 7:
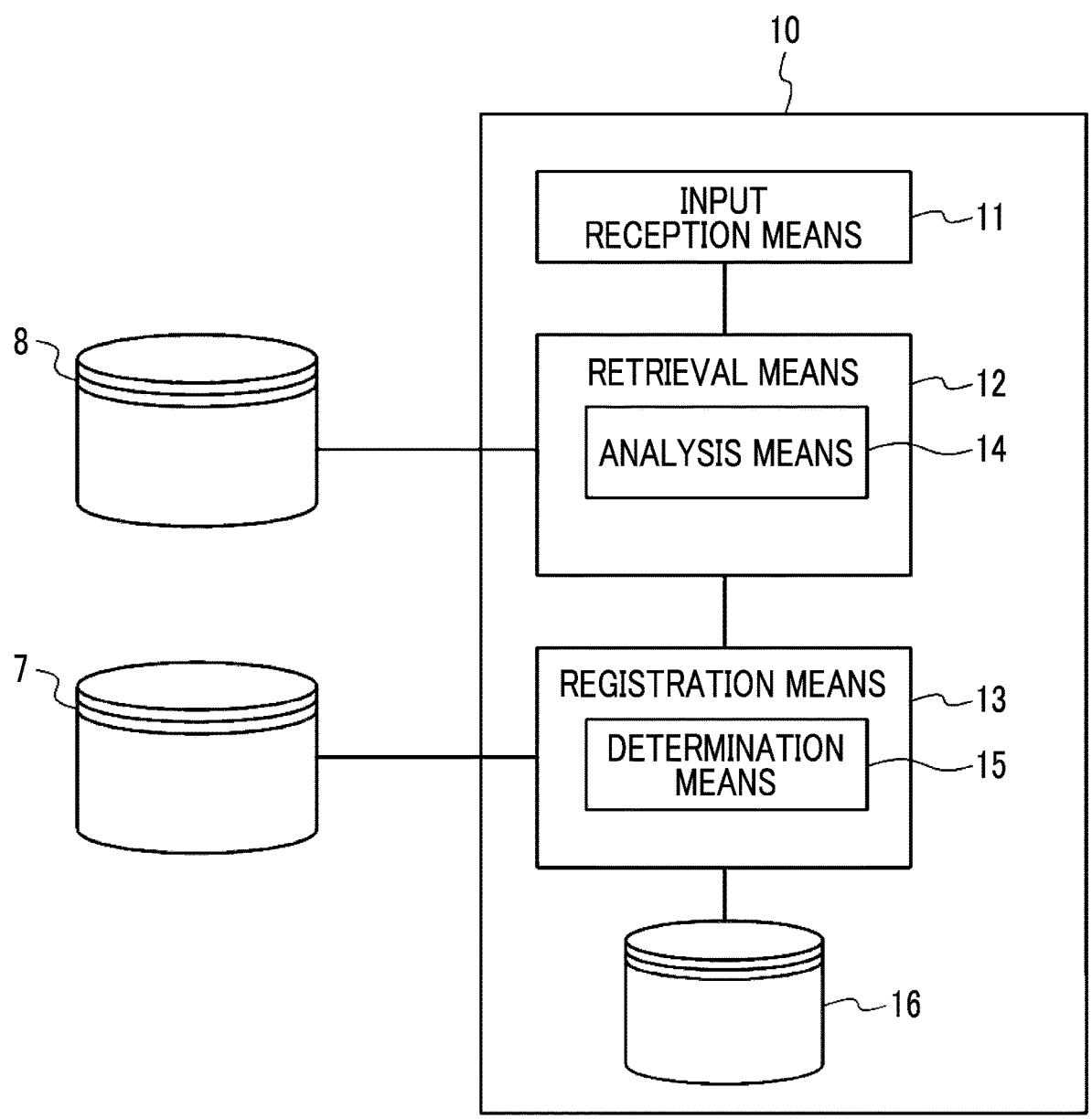
FIG. 7 is a diagram showing a schematic configuration of a learning data generation support apparatus.

As shown in FIG. 7, the learning data generation support apparatus 10 includes input reception means 11, retrieval means 12, and registration means 13.

The input reception means 11 receives an input of a retrieval keyword through an input device such as a keyboard. For example, as the retrieval keyword, a name of an organ such as the "lung", the "liver", the "kidneys", the "heart", the "large intestine", the "bronchus", or a "blood vessel", or a disease name or a symptom such as "lung cancer", "liver cancer", "pleural effusion", "nodules", or "aortic aneurysm" may be input. One retrieval keyword may be used, or two or more retrieval keywords may be used. For example, inputs of two or more retrieval keywords such as the "lung" and "nodules" may be received.

The retrieval means 12 includes analysis means 14 that analyzes a character string of an interpretation report, and retrieves an interpretation report corresponding to a retrieval keyword from interpretation reports stored in the interpretation report database 8.

The analysis means 14 divides sentences in the interpretation report into words using natural language analysis, and analyzes the interpretation report on the basis of arrangement of the words to analyze the content of the interpretation report. It is preferable to perform the analysis on the basis of the dictionary table 57 (see FIGS. 4 and 5) used in input of the report, and the analysis is performed on the basis of a combination of character strings corresponding to organs in an upper layer of a hierarchical structure and doctor's opinion elements in a lower layer thereof. For example, the content of the interpretation report is analyzed on the basis of whether a character string relating to the doctor's opinion element "margin", "surface", the "degree of tumefaction" or "tumefaction portion" of the doctor's opinion item the "type of the liver" is present subsequent to the "liver", "bile ducts", or the like that matches an organ in the dictionary table, a combination of a character string indicating the degree and a character string indicating arrangement and units of numbers, and a combination of a character string indicating a portion in each organ and a character string relating to an expression that connecting them.

For example, in a case where the "liver" and the "tumefaction of the left lobe" are designated as retrieval keywords, the retrieval means 12 analyzes character strings using the analysis means 14 to retrieve an interpretation report in which a sentence that affirms the tumefaction of the left lobe of the liver, for example, "The left lobe of the liver is lightly tumefacient." is recorded as an interpretation report corresponding to the retrieval keywords.

Further, as the retrieval keywords, a character string indicating a lesion may be included. With respect to the lesion, similar to an organ, a lesion such as "pulmonary nodules" and terms indicating its features are divided into a hierarchy to be registered in the dictionary table 57. Further, using the dictionary table 57, from a combination of a character string relating to a lesion type, a lesion shape, and the like, a character string indicating the degree, and a character string indicating arrangement and units of numbers, and a combination of character strings relating to expressions that connect them, an interpretation report in which the content relating to the size and shape of a lesion portion is recorded may be retrieved.

For example, in a case where a lesion name "pulmonary nodules" and "spicular" that is a feature thereof are designated as retrieval keywords, the retrieval means 12 retrieves an interpretation report in which "Spicular pulmonary nodules are seen" is recorded as an interpretation report corresponding to the retrieval keywords, for example.

Further, the retrieval keywords may include a character string indicating a state of cancer, for example, a stage indicating the degree of progression of the cancer, or metastasis or non-metastasis. Alternatively, the retrieval keywords may include the type of cancer. The type of cancer is "lung cancer", "liver cancer", "kidney cancer", "heart cancer", "large intestine cancer", or the like. Further, the "large intestine cancer" may be divided into "colon cancer" and "rectal cancer". In this way, in the case of cancer with each organ name, it is possible to specify a location where the cancer is present by analyzing the character string by the analysis means 14.

The retrieval keywords to be retrieved may be a character string that means a change of a state of an anatomic region that is present in two or more medical images obtained by imaging the same patient at different times. The character string indicating comparison of the anatomic regions may include a character string indicating a change in size of an organ itself, the presence or absence of a lesion in an organ region, and a change in size of the lesion, or the like, which may be any string that means information obtained by comparing the anatomic regions.

For example, the retrieval keywords may be a character string that means a change of a lesion obtained by comparing a lung region of a previous image with a lung region of a current image, such as "enlargement of the size of a pulmonary nodule". In this case, for example, the retrieval means 12 retrieves an interpretation report in which "the size of a pulmonary nodule of the right upper lobe is enlarged" as an interpretation report corresponding to the retrieval keywords.

As described above, by designating a character string that means a feature of an anatomic region, the presence of a lesion, or comparison of anatomic regions as the retrieval keywords, retrieving an interpretation report in which the content corresponding to a meaning of such a character string is included, and extracting a medical image corresponding to the retrieved interpretation report, it is possible to retrieve an image having a high possibility of being a medical image to be retrieved from the image database 7.

Further, the registration means 13 includes determination means 15, and determines whether a medical image corresponding to a retrieved interpretation report is suitable for correct answer data, and registers the medical image determined to be suitable and a mask image thereof as correct answer data.

The determination means 15 first performs image processing with respect to a retrieved medical image to extract an anatomic region related to a retrieval keyword. In a case where the size of the extracted anatomic region is different from a standard size of the anatomic region, that is, in a case where the size of the anatomic region deviates from a range of the standard size, the determination means 15 determines that the medical image is suitable for correct answer data. Alternatively, in a case where the shape of the extracted anatomic region is different from a standard shape of the anatomic region, that is, in a case where the shape of the anatomic region deviates from a range of the standard shape, the determination means 15 determines that the medical image is suitable for correct answer data.

For example, in a case where the "liver" and the "tumefaction of the left lobe" are designated as retrieval keywords, an extraction process of the liver is performed from a medical image, and then, extraction of the left lobe is performed. With respect to the extracted left lobe of the liver, it is determined whether the size of a corresponding region is within a range of a standard size or deviates from the range of the standard size. Alternatively, it is determined whether the shape of the extracted left lobe of the liver is within a range of a standard shape or deviates from the range of the standard shape.

The determination of whether the size of an organ region is within a range of a standard size or deviates from the standard size is performed on the basis of the size of the organ region of a medical image that is designated as a reference image in advance. For example, a plurality of images obtained by imaging an organ of a standard size are designated as reference images, and then, an organ of a size in a predetermined range from an average value of the sizes of the organ extracted from the plurality of images designated as the reference images or a representative value of the sizes is set to have a standard size, and an organ of a size that deviates from the range is set to deviate from the standard size. Similarly, the shape of an organ having a difference in a predetermined range from an average shape of the shapes of the organ extracted from the plurality of images designated as the reference images is set as a standard shape, and an organ of a shape that deviates from the range is set to deviate from the standard shape. For example, in comparing an organ region extracted from a medical image with a standard shape in an overlapping manner, in a case where the area or volume of the organ region that does not overlap the standard shape is within a reference value, it is determined that the organ region has the standard shape, and in a case where the area or volume is equal to or greater than the reference value, it is determined that the organ region deviates from the standard shape.

As information relating to the standard size of the organ region, for example, the volume of the organ region, the length in a carniocaudal direction (or a length direction) of the organ region, or the like may be used. Further, as information relating to the standard shape of the organ region, for example, a land mark position, or the like may be used. The information relating to the standard size and the standard shape of the organ region is stored in the image database 7 in advance. In a case where one organ can be divided into a plurality of sections, such as a lung field or the liver, information of a standard size or a standard shape may be stored for each section. For example, the lung field may be divided into the upper right lobe, the right middle lobe, the lower right lobe, the upper left lobe, and the lower left lobe, and information of a standard volume, a standard length, a standard land mark, or the like may be stored. The liver may be divided into the right lobe and the left lobe, and information of a standard volume, a standard length, a standard land mark, or the like may be stored.

Figure 8A:
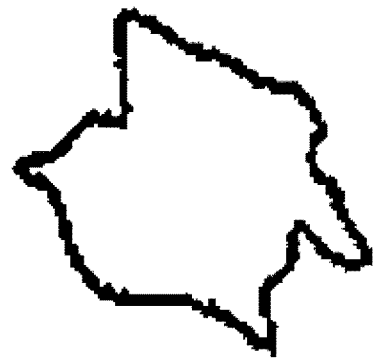
FIG. 8A is a diagram for illustrating a first exemplary anatomic region.
Figure 8B:
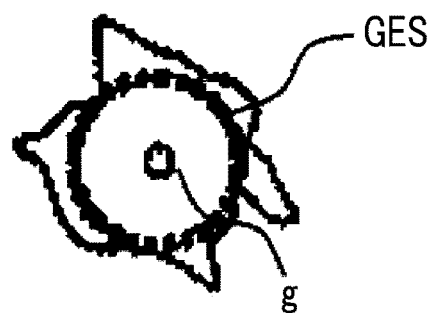
FIG. 8B is a diagram for illustrating a second exemplary anatomic region.
Figure 8C:
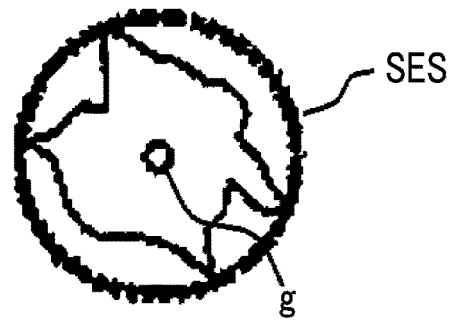
FIG. 8C is a diagram for illustrating a third exemplary anatomic region.

Determination of whether the shape of a lesion region is a standard shape or deviates from the standard shape may be performed on the basis of a plurality of pieces of information indicating features of a lesion. For example, as shown in FIGS. 8A to 8C, features of lung cancer are indicated by the length and the radius of a pulmonary nodule, a greatest enclosed sphere (GES) included in the pulmonary nodule centering around the center of gravity g of the pulmonary nodule, and a smallest enclosing sphere (SES) including all of the pulmonary nodule features (pointed protrusions) centering around the center of gravity g of the pulmonary nodule, and features of its shape are determined by the number of protrusions included in the greatest enclosed sphere (GES), a difference between the radius of the greatest enclosed sphere (GES) and the radius of the smallest enclosing sphere (SES), and the like. Since most pulmonary nodules have shapes close to a circle, shade and shadow close to a circle may be set as a standard shape, and a shape having a large number of spiculas may be determined as a shape that deviates from the circle.

In the above description, data used for determination of a standard size or a standard shape of an anatomic region may be appropriately determined according to features of the anatomic region.

Further, medical images of which anatomic regions have sizes or shapes different from a standard size or shape may be in advance collected from medical images stored in the image database 7, the collected medical images may be classified into a plurality of classes through a clustering process, and a medical image disposed at the center of each cluster may be picked up, so that a desired medical image can be extracted from a small number of medical images. For example, in selecting an image of which the size of an anatomic region deviates from a standard size, the clustering process is executed using numerical values such as the volume of an organ region and the length in the carniocaudal direction of the organ region, calculated from each image as feature values, and using a method such as k-means method. In a case where there are a large number of images of which the sizes deviate from the standard size, by picking up only a predetermined number of (for example, 20, or the like) images from each cluster on the basis of a result of the clustering process, it is possible to efficiently select images necessary for correct answer data with a small number of images.

The registration means 13 registers a medical image for which it is determined by the determination means 15 that the size of an anatomic region is different from a standard size of the anatomic region, or a medical image for which it is determined that the shape of the anatomic region is different from a standard shape of the anatomic region in the storage 16 as correct answer data together with a mask image thereof. The storage 16 is formed of a large capacity storage device for storing images.

Alternatively, only image IDs may be registered in the storage 16, and may be read out from the image database 7 when used in learning.

Figure 9:
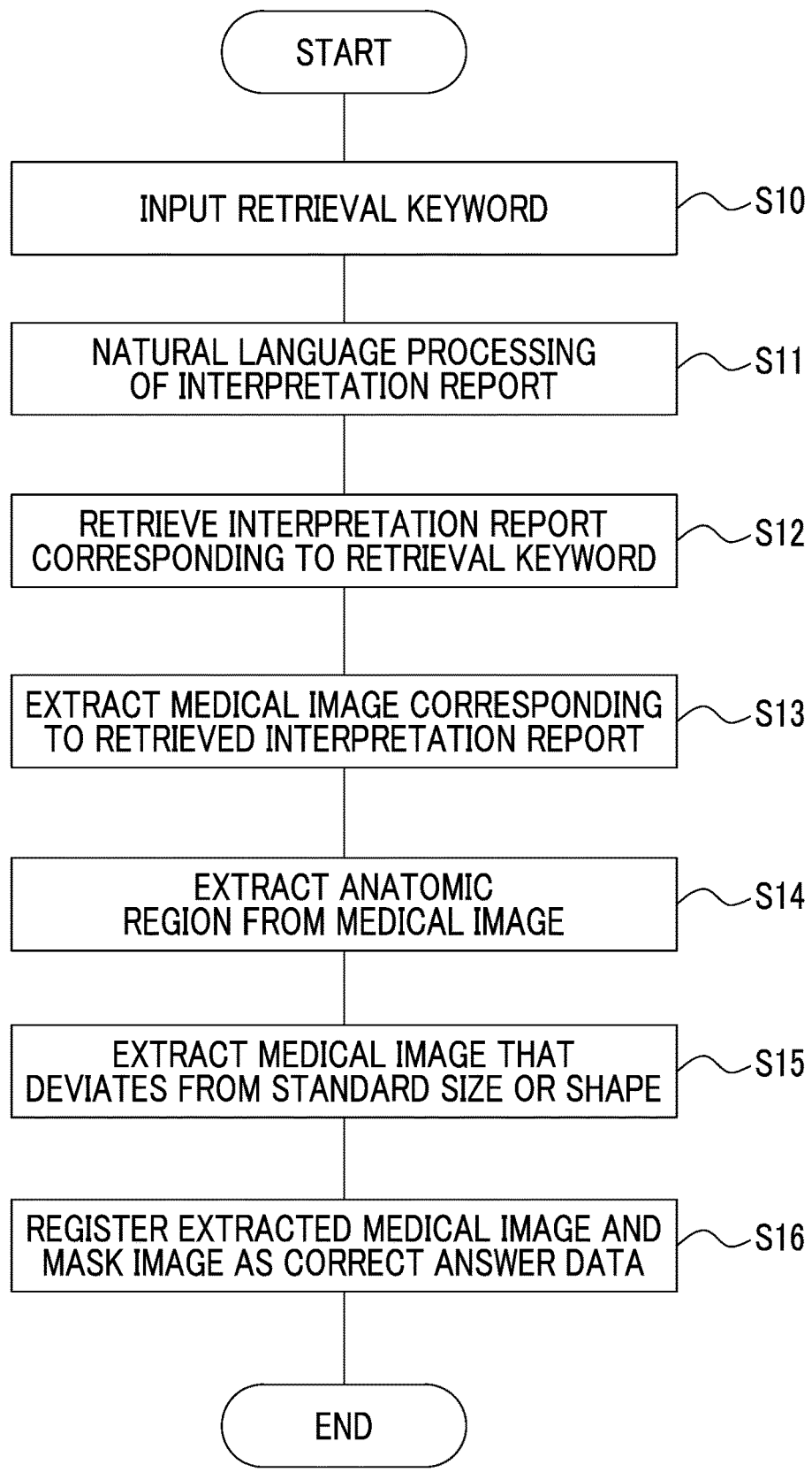
FIG. 9 is a flowchart showing a flow of a process of the learning data generation support apparatus.

Hereinafter, with respect to a flow of processes of the learning data generation support apparatus 10 with the above-mentioned configuration, a registration method of correct answer data will be described in detail with reference to an example of an organ region using a flowchart in FIG. 9.

First, in a case where the "liver" and the "tumefaction of the left lobe" are input through an input device such as a keyboard as retrieval keywords, the input reception means 11 receives the retrieval keywords (S10). The retrieval means 12 executes natural language analysis with respect to interpretation reports stored in the interpretation report database 8 by the analysis means 14 (S11) to retrieve an interpretation report corresponding to the retrieval keywords (S12).

The determination means 15 first extracts a medical image corresponding to the retrieved interpretation report from the image database 7 (S13), and then, performs image processing with respect to the medical image to extract the left lobe of the liver as an anatomic region related to the retrieval keywords (S14). The determination means 15 determines whether the volume of the left lobe of the liver of each medical image deviates from a standard size, and extracts a medical image in which the left lobe of the liver that deviates from the standard size is present (S15).

The registration means 13 registers the medical image determined to deviate from the standard range by the determination means 15, and a mask image thereof in the storage 16 as correct answer data (S16).

In a case where a plurality of pieces of correct answer data, instead of one piece of correct answer data, are to be learned, S12 to S16 are repeated with the registered medical image being excluded to register a desired number of pieces of correct answer data.

Next, a registration method of correct answer data will be described in detail with reference to an example of a pulmonary nodule using the flowchart in FIG. 9.

First, in a case where the "pulmonary nodule" and the "spicular" are input through an input device such as a keyboard as retrieval keywords, the input reception means 11 receives the retrieval keywords (S10). The retrieval means 12 executes natural language analysis with respect to interpretation reports stored in the interpretation report database 8 by the analysis means 14 (S11) to retrieve an interpretation report corresponding to the retrieval keywords (S12).

The determination means 15 first extracts a medical image corresponding to the retrieved interpretation report from the image database 7 (S13), and then, performs image processing with respect to the medical image to extract a lung field region related to the retrieval keywords and to then extract a pulmonary nodule (S14). The determination means 15 determines whether the extracted pulmonary nodule of each medical image has a large number of spiculas to deviate from a range of a standard shape, and extracts a medical image in which the pulmonary nodule that deviates from the standard shape is present (S15).

The registration means 13 registers the medical image determined to deviate from the standard range by the determination means 15, and a mask image thereof in the storage 16 as correct answer data (S16).

In a case where a plurality of pieces of correct answer data, instead of one piece of correct answer data, are to be learned, S12 to S16 are repeated with the registered medical image being excluded to register a desired number of pieces of correct answer data.

As shown in FIG. 10, the medical images and the mask images of the registered correct answer data are displayed as a list. By displaying the list in this way, it is possible to confirm which medical image is to be learned.

In a case where the learning is performed, machine learning based on a neural network may be performed using the correct answer data registered in the storage 16. Specifically, for example, by using a convolutional neural network or the like, it is possible to generate an image recognition device.

As described in detail above, an interpretation report is retrieved using a specific retrieval keyword to retrieve a medical image including an anatomic region having a high possibility of deviating from a standard anatomic region, and an anatomic region is detected from an actual medical image to register a medical image that deviates from the standard anatomic region as correct answer data. In this way, by registering a medical image having an anatomic region that deviates from a standard size of the anatomic region or a medical image having an anatomic region that deviates from a standard shape of the anatomic region as correct answer data and performing learning, it is possible to appropriately differentiate even a medical image in which the anatomic region that deviates from the standard size or shape is present.

In the above-described embodiment, a case where a general-purpose computer connected to the network 9 functions as the learning data generation support apparatus 10 has been described, but a configuration in which a learning data generation support program is installed in the radiologist workstation 3 so that the radiologist workstation 3 functions as the learning data generation support apparatus 10 may be used.

Further, a configuration in which the determination means 15 is provided in the image database 7 and the learning data generation support apparatus 10 does not request transmission of a medical image corresponding to an interpretation report retrieved by the retrieval means 12 from the image database 7, but instead, receives a determination result from the image database 7, and then, requests transmission of a medical image only when the determination result is determined to be suitable for correct answer data may be used.

Alternatively, a configuration in which a medical image corresponding to an interpretation report retrieved by the retrieval means 12 of the learning data generation support apparatus 10 is transmitted to a computer exclusive for image processing, image processing is performed by the computer exclusive for image processing, and a result of the image processing is received therefrom may be used. Further, a configuration in which the computer exclusive for image processing performs a determination process (corresponding to the determination means) and a determination result is received therefrom may be used.

As described above, all the functions of the learning data generation support apparatus 10 may not be provided on one computer, but may be divided into a plurality of computers.

As specifically described above, it is possible to acquire a large amount of various correct answer data necessary for machine learning using images stored in a medical image management system.

What is claimed is:

1. A machine learning data generation support apparatus comprising:
 a processor configured to:
  retrieve an interpretation report, in which a character string that corresponds to a retrieval keyword is included, from a plurality of interpretation reports by analyzing character strings included in each of the plurality of interpretation reports by using natural language analysis, the retrieval keyword being a name of an organ, a name of a disease, or a name of a symptom;

extract an anatomic region related to the retrieval keyword from a medical image corresponding to the retrieved interpretation report by performing image processing on the medical image; and register anatomic region information and the medical image thereof as correct answer data for machine learning, the anatomic region information indicating a range or a position of the extracted anatomic region from the medical image, in a case where the size of the extracted anatomic region deviates from a range of a standard size of the anatomic region or in a case where the shape of the extracted anatomic region deviates from a range of a standard shape of the anatomic region.

2. The machine learning data generation support apparatus according to claim 1, wherein the processor determines whether or not the size of the extracted anatomic region is different from the standard size of the anatomic region on the basis of the size of an anatomic region of a medical image that is set as a reference image in advance, or determines whether or not the shape of the extracted anatomic region is different from the standard shape of the anatomic region on the basis of the shape of an anatomic region of a medical image that is set as a reference image in advance.

3. The machine learning data generation support apparatus according to claim 1, wherein the processor executes natural language analysis with respect to the interpretation report to extract information relating to the size or shape of the anatomic region.

4. The machine learning data generation support apparatus according to claim 1, wherein the retrieval keyword includes a character string that means a change of a state of the anatomic region that is present in two or more medical images obtained by imaging the same patient at different times.

5. The machine learning data generation support apparatus according to claim 1, wherein the retrieval keyword is a character string indicating a state of a cancer.

6. The machine learning data generation support apparatus according to claim 1, wherein the anatomic region is any one of the lung, the liver, the kidneys, the heart, and the large intestine.

7. The machine learning data generation support apparatus according to claim 1, wherein the anatomic region is a region of a cancer.

8. The machine learning data generation support apparatus according to claim 7, wherein the retrieval keyword includes the kind of the cancer.

9. The machine learning data generation support apparatus according to claim 1, wherein the medical image is an MM image, a CT image, a simple X-ray image, or an ultrasound image.

10. The machine learning data generation support apparatus according to claim 1, the processor being further configured to:

receive an input of the retrieval keyword, wherein the processor retrieves the interpretation report in which the input retrieval keyword is included.

11. The machine learning data generation support apparatus according to claim 1, the processor being further configured to:

determine that the anatomic region and the medical image are used as correct answer data for machine learning in a case where the size of the extracted anatomic region is different from a standard size of the anatomic region or in a case where the shape of the extracted anatomic region is different from a standard shape of the anatomic region.

12. The machine learning data generation support apparatus according to claim 1, wherein:

in case where the anatomical region is an organ, the processor determines that a size of the organ deviates from a standard size, when the size of the organ has a different size from a predetermined range or more from an average value or a representative value of sizes of organs extracted from a plurality of images designated as the reference images, or in a case where the anatomical region is an organ, the processor determines that the organ region deviates from the standard shape, when an area or a volume of the organ region that does not overlap an average shape of the organ extracted from the plurality of images designated as the reference images is equal to or greater that the reference value, or in a case where the anatomical region is a lesion region, the processor determines whether a shape of the lesion region deviates from a standard shape based on a plurality of pieces of information indicating features of a lesion.

13. An operation method of a machine learning data generation support apparatus, comprising:

retrieving an interpretation report, in which a character string that corresponds to a retrieval keyword is included, from a plurality of interpretation reports by analyzing character strings included in each of the plurality of interpretation reports by using natural language analysis, the retrieval keyword being a name of an organ, a name of a disease, or a name of a symptom;

extracting an anatomic region related to the retrieval keyword from a medical image corresponding to the retrieved interpretation report by performing image processing on the medical image; and registering anatomic region information and the medical image thereof as correct answer data for machine learning, the anatomic region information indicating a range or a position of the extracted anatomic region from the medical image, in a case where the size of the extracted anatomic region deviates from a range of a standard size of the anatomic region or in a case where the shape of the extracted anatomic region deviates from a range of a standard shape of the anatomic region.

14. A non-transitory computer-readable recording medium storing therein a machine learning data generation support program for causing a computer to:

retrieve an interpretation report, in which a character string that corresponds to a retrieval keyword is included, from a plurality of interpretation reports by analyzing character strings included in each of the plurality of interpretation reports by using natural language analysis, the retrieval keyword being a name of an organ, a name of a disease, or a name of a symptom;

extract an anatomic region related to the retrieval keyword from a medical image corresponding to the retrieved interpretation report by performing image processing on the medical image; and register anatomic region information and the medical image thereof as correct answer data for machine learning, the anatomic region information indicating a range or a position of the extracted anatomic region from the medical image, in a case where the size of the extracted anatomic region deviates from a range of a standard size of the anatomic region or in a case where the shape of the extracted anatomic region deviates from a range of a standard shape of the anatomic region.

* * * * *